United States Patent
Schmidt et al.

(10) Patent No.: US 10,980,436 B2
(45) Date of Patent: Apr. 20, 2021

(54) SYSTEMS, METHODS, AND DEVICES FOR USING PASSIVE PRESSURE SENSORS TO MEASURE PRESSURE AT AN INACCESSIBLE LOCATION

(71) Applicant: Duke University, Durham, NC (US)

(72) Inventors: Allison L. Schmidt, Durham, NC (US); Cameron R. Bass, Durham, NC (US); Carrie R. Muh, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 449 days.

(21) Appl. No.: 16/073,465

(22) PCT Filed: Feb. 1, 2017

(86) PCT No.: PCT/US2017/016077
§ 371 (c)(1),
(2) Date: Jul. 27, 2018

(87) PCT Pub. No.: WO2017/136461
PCT Pub. Date: Aug. 10, 2017

(65) Prior Publication Data
US 2019/0038160 A1 Feb. 7, 2019

Related U.S. Application Data

(60) Provisional application No. 62/289,413, filed on Feb. 1, 2016.

(51) Int. Cl.
*A61B 5/03* (2006.01)
*A61B 5/00* (2006.01)
(Continued)

(52) U.S. Cl.
CPC ............ *A61B 5/031* (2013.01); *A61B 5/6862* (2013.01); *A61B 7/04* (2013.01); *A61M 27/006* (2013.01);
(Continued)

(58) Field of Classification Search
CPC .......... A61B 5/031–032; A61B 5/6862; A61B 2562/0204; A61B 2562/0247;
(Continued)

(56) References Cited

U.S. PATENT DOCUMENTS 5,873,840 A * 2/1999 Neff .................. A61B 5/031
343/767
2005/0182463 A1 8/2005 Hunter et al.
(Continued)

OTHER PUBLICATIONS

International Search Report and Written Opinion for International Application No. PCT/US2017/016077, dated May 24, 2017.(9 pages).

*Primary Examiner* — Daniel L Cerioni
*Assistant Examiner* — Raymond P Dulman
(74) *Attorney, Agent, or Firm* — Quarles & Brady LLP

(57) ABSTRACT

In some embodiments, systems, methods and devices for using passive pressure sensors to measure pressure at an inaccessible location are provided. In some embodiments, a system for determining pressure in a ventriculoperitoneal shunt implanted in a subject is provided, the system comprising: an acoustic source emitting signals over a range of frequencies; the ventriculoperitoneal shunt, comprising: a lumen that provides a conduit for cerebrospinal fluid between; and a passive acoustic element in a wall of the ventriculoperitoneal shunt filled with a gas, wherein the passive acoustic element emits a second signal at a resonant frequency that varies based on the pressure on the passive acoustic element; an acoustic receiver that detects the second signal and outputs an electrical signal that represents at
(Continued)

least the resonant frequency; and a processor programmed to: receive the electrical signal; determine the pressure using the resonant frequency; and present the pressure using a display.

12 Claims, 10 Drawing Sheets

(51) Int. Cl.
*A61B 7/04* (2006.01)
*A61M 27/00* (2006.01)

(52) U.S. Cl.
CPC .............. *A61B 2562/0204* (2013.01); *A61B 2562/0247* (2013.01); *A61M 2205/3344* (2013.01); *A61M 2205/3375* (2013.01); *A61M 2205/502* (2013.01); *A61M 2210/0693* (2013.01); *A61M 2210/1017* (2013.01)

(58) Field of Classification Search
CPC ........ A61M 27/006; A61M 2205/3344; A61M 2205/3375; A61M 2210/0693; A61M 2210/1017
See application file for complete search history.

(56) References Cited

U.S. PATENT DOCUMENTS

| | | |
|---|---|---|
| 2006/0020239 A1 | 1/2006 | Geiger et al. |
| 2011/0036173 A1 | 2/2011 | Chommeloux et al. |
| 2014/0243703 A1 | 8/2014 | Schmidt et al. |
| 2014/0309532 A1* | 10/2014 | Bedell .................. A61B 8/0891 600/449 |

* cited by examiner

SYSTEMS, METHODS, AND DEVICES FOR USING PASSIVE PRESSURE SENSORS TO MEASURE PRESSURE AT AN INACCESSIBLE LOCATION

CROSS-REFERENCE TO RELATED APPLICATIONS

This application represents the national stage entry of International Application PCT/US2017/016077 filed Feb. 1, 2017, which claims the benefit of U.S. Provisional Application 62/289,413, filed Feb. 1, 2016, which is hereby incorporated by reference herein in its entirety.

STATEMENT REGARDING FEDERALLY SPONSORED RESEARCH

N/A

BACKGROUND

In areas of medicine and medical research, it is often desirable to monitor the pressure within the body. In particular, treatment of neurological conditions often involves the careful monitoring and treatment of changes in intracranial pressure (ICP). The ICP refers to the pressure within the skull, which can become elevated due to trauma or disease. Increased ICP can be a serious or life-threatening condition, and medical practitioners often need to take steps to decrease the ICP.

One such condition is hydrocephalus, a state that occurs when there is an overaccumulation of the fluid surrounding the brain and spinal cord. That fluid is called cerebrospinal fluid ("CSF"). Hydrocephalus is often treated with an implanted device called a shunt to allow excess CSF to drain. At one end, a catheter is implanted within the CSF-filled space, generally within the space in the brain called the ventricle. Tubing then allows the excess CSF to flow to another region of the body, such as the peritoneal space, where the fluid can be resorbed. Often, shunts include devices like programmable or non-programmable valves, anti-siphon devices, and flow-regulating devices which are used to control the flow of fluid.

Although shunts are critical in managing hydrocephalus, they fail at a tremendously high rate: one third of pediatric patients with shunts require surgery to revise or replace the shunt within the first year. Common reasons for failure include the shunt becoming clogged where the CSF enters or exits the shunt, or at a valve mechanism. It is often not possible to determine whether the shunt is operating correctly without resorting to invasive measures such as shunt taps or exploratory surgery.

Intracranial pressure sensors in current use typically attach to wires that pass through the skull and skin to connect to an external monitor; these are only temporary measures used for a few days or weeks at a time. Implantable systems have previously been proposed to measure pressure, both intracranially and within shunts. However, none have been adopted clinically. These methods often require relatively complex machinery, such as electronics which must be implanted and powered, and pressure transducers whose measurements drift over time.

It is desirable to provide passive pressure sensors and methods of making and using same.

SUMMARY

In accordance with some embodiments of the disclosed subject matter, a system for determining pressure in a ventriculoperitoneal shunt implanted in an in vivo subject is provided, the system comprising: an acoustic source that emits a plurality of first signals over a range of frequencies; the ventriculoperitoneal shunt, comprising: at least one lumen that provides a conduit for cerebrospinal fluid between an area of the subject's brain and a cavity within the body of the subject; and a passive acoustic element in a wall of the ventriculoperitoneal shunt comprising a void in the wall of the ventriculoperitoneal shunt that is filled with a gas, wherein the passive acoustic element emits a second signal at a resonant frequency that varies based on the pressure on the passive acoustic element in response to receiving a signal of the plurality of first signals at the resonant frequency; an acoustic receiver that detects the second signal and outputs an electrical signal that represents at least the resonant frequency; and at least one hardware processor that is programmed to: receive the electrical signal; determine the pressure on the passive acoustic element using at least the resonant frequency; and present the pressure using a display.

In some embodiments, the passive acoustic element has a substantially spherical shape.

In some embodiments, the passive acoustic element has an elongate shape.

In some embodiments, the gas is comprised primarily of nitrogen gas.

In some embodiments, the ventriculoperitoneal shunt further comprises a second passive acoustic element, wherein the second passive acoustic element emits a third signal at a second resonant frequency that varies based on the pressure on the passive acoustic element in response to receiving a signal of the plurality of signals at the second resonant frequency, wherein the properties of the second passive acoustic element are different than the properties of the passive acoustic element, wherein the acoustic source emits a plurality of fourth signals over a second range of frequencies that does not overlap with the range of frequencies, and wherein the hardware processor is further programmed to: detect a third signal at a second resonant frequency; determine the pressure on the second passive acoustic element using at least the second resonant frequency.

In some embodiments, the acoustic source is a speaker and the first frequency is between 20 Hz and 20 kHz.

In accordance with some embodiments of the disclosed subject matter, a method for determining pressure in a ventriculoperitoneal shunt implanted in an in vivo subject is provided, the method comprising: emitting, using an acoustic source, a plurality of first signals over a range of frequencies toward the ventriculoperitoneal shunt, the ventriculoperitoneal shunt comprising: at least one lumen that provides a conduit for cerebrospinal fluid between at least an area of the subject's brain and a cavity within the body of the subject; and a passive acoustic element in a wall of the ventriculoperitoneal shunt comprising a void in the wall of the ventriculoperitoneal shunt that is filled with a gas, wherein the passive acoustic element emits a second signal at a resonant frequency that varies based on the pressure on the passive acoustic element in response to receiving a signal of the plurality of first signals at the resonant frequency; detecting, using an acoustic receiver, the second signal; output, using the acoustic receiver, an electrical signal that represents at least the resonant frequency; determine the pressure on the passive acoustic element using at least the resonant frequency; and present, using a display, the pressure.

In accordance with some embodiments of the disclosed subject matter, a passive pressure sensor device is provided, comprising: a plurality of passive acoustic elements that each emits a response signal at a resonant frequency in response to receiving an applied signal at the resonant frequency, wherein the value of the resonant frequency varies based on the pressure on the passive acoustic element emitting the second signal; a first material filling each of the plurality of passive acoustic elements; and a second material surrounding the first material of each of the plurality of passive acoustic elements.

In some embodiments, the first material comprises primarily a gas.

In some embodiments, the gas comprises primarily nitrogen gas.

In some embodiments, the gas comprises primarily sulfur hexafluoride gas.

In some embodiments, each of the plurality of passive acoustic elements have substantially the same dimensions, and the value for the second frequency emitted by each of the plurality of passive acoustic elements is substantially the same.

In some embodiments, the resonant frequency is in the acoustic range.

In some embodiments, the value of the resonant frequency increases as pressure on the passive acoustic element increases.

In some embodiments, the surrounding material is a compliant material.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1A:
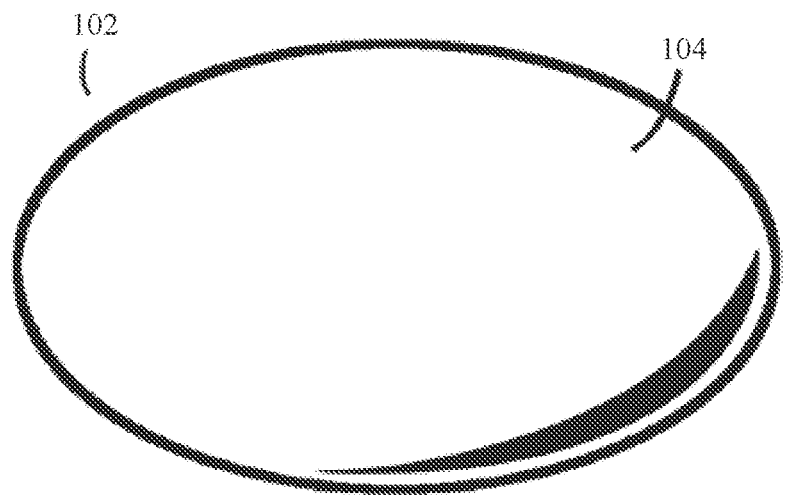
FIGS. 1A and 1B show an example of a passive pressure sensor device in accordance with some embodiments of the disclosed subject matter.

For the purposes of promoting an understanding of the principles of the disclosed subject matter, reference will now be made to embodiments of the mechanisms described herein using specific language. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

As used herein, the term "subject" and "patient" are used interchangeably and refer to any animal being examined, studied or treated. It is not intended that the present disclosure be limited to any particular type of subject. In some embodiments of the present invention, humans are the preferred subject, while in other embodiments nonhuman animals are the preferred subject, including but not limited to mice, monkeys, ferrets, cattle, sheep, goats, pigs, chicken, turkeys, dogs, cats, horses and reptiles. In certain embodiments, the subject is suffering from a neurological condition, such as hydrocephalus.

Unless otherwise defined, all technical terms used herein have the same meaning as commonly understood by one of ordinary skill in the art to which this disclosure belongs.

In accordance with various embodiments, mechanisms (which can, for example, include systems, methods and devices) for using passive pressure sensors to measure pressure at an inaccessible location are provided.

In some embodiments, the mechanisms described herein can facilitate the measurement of a pressure using a passive acoustic element that emits an acoustic signal at a frequency that is dependent on the pressure being exerted on the passive acoustic element. For example, a shunt can include one or more passive acoustic elements that can emit an acoustic signal with a frequency that depends on the pressure being exerted on the passive acoustic elements (e.g., by fluid in the shunt). In such an example, if the shunt becomes blocked, the pressure in the shunt can increase, thereby causing the frequency of the acoustic signal emitted by the passive acoustic elements to change.

In some embodiments, the mechanisms described herein can be used to determine the pressure in an inaccessible location based on the frequency of a signal emitted by a passive acoustic element. For example, based on a relationship between pressure at the passive acoustic elements in the shunt and the frequency of a signal emitted by that passive acoustic element, the mechanisms described herein can be used to determine that the pressure within the shunt has increased.

In some embodiments, the mechanisms described herein can emit an acoustic signal that can cause one or more passive acoustic elements to emit an acoustic signal that is indicative of pressure at the passive acoustic element. For example, a speaker can be used to emit an acoustic signal toward the passive acoustic elements in the shunt at a frequency that causes the passive acoustic elements to emit an acoustic signal with a frequency that changes with pressure, and therefore can be used to determine the pressure at the passive acoustic sensors.

Figure 1B:
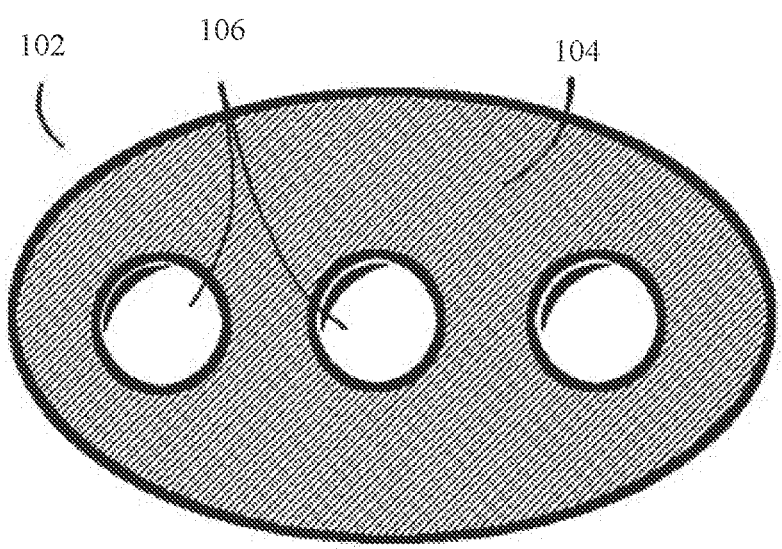

FIGS. 1A and 1B show an example of a passive pressure sensor device 102 in accordance with some embodiments of the disclosed subject matter. In such embodiments, one or more passive acoustic elements 106 can be surrounded by a material 104. In some embodiments, each of the passive acoustic elements 106 can be a void within the surrounding material 104 that can be filled with any suitable material, such as a fluid, a gas, a gel, etc. For example, in some embodiments, the passive acoustic elements 106 can be filled with an inert gas, such as nitrogen, sulfur hexafluoride, helium, argon, neon, krypton, xenon, radon, carbon dioxide, etc. Additionally, in some embodiments in which the passive pressure sensor device 102 is configured to be implanted in a living subject, gas used to fill the passive acoustic elements 106 can be biologically inert as such as nitrogen, sulfur hexafluoride, argon, helium, carbon dioxide, etc.

As another example, the passive acoustic elements 106 can be filled with a substantially non-compressible fluid, such as, water, silicon oil formulations, etc. As yet another example, the passive acoustic elements 106 can be filled with a non-compressible gel within the void in the surrounding material 104, such as, gelatin, agarose, a naturally occurring gel, a polymer based synthetic gel, a cross-linked polymer based gel, a hydrogel, a lipogel, a hydrophobic gel, a hydrophilic gel, any other suitable type of gel, or any suitable combinations thereof. In some embodiments, the passive acoustic elements 106 can include a piezoelectric element.

In some embodiments, for example, as described below in connection with FIGS. 2 and 9-12, the passive acoustic elements 106 can receive acoustic signals from a source external to the passive acoustic elements 106, and can resonate in response to receiving a signal at a particular frequency (and potentially other frequencies, such as harmonics of the second frequency) that varies with pressure on the passive acoustic elements 106. For example, when the acoustic signal at the resonant frequency impinges on the passive acoustic element 106, the passive acoustic element can be acoustically excited, which can cause the passive acoustic element 106 to vibrate and emit an acoustic signal at the resonant frequency. In such an example, the value of the frequency that excites the passive acoustic element 106 can vary based on the pressure currently being exerted on the passive acoustic element, among other factors. In some embodiments, in addition to varying with pressure, the resonant frequency of the passive acoustic elements 106 can also depend on properties of the material filling the passive acoustic elements 106, the amount of material and/or the density of the material filling the passive acoustic elements 106, the temperature of the passive acoustic elements, etc. As another example, the response of a material at a frequency in the acoustic range can be much different than the response at frequencies in the ultrasonic range. In some embodiments, rather than the acoustic signal being a signal at a particular frequency, the signal can be an impulse that contains many frequencies.

In some embodiments, the pressure determined based on frequency can be modified based on conditions at the location at which the measurements were carried out. For example, differences in atmospheric pressure can have an effect on the measured pressure, and can thus bias the results of the determination. Such a bias in the results can, for example, lead to erroneous determinations that there have been changes at the location of the passive acoustic element(s) 106 being measured across two measurements at different times and/or geographic locations, when the changes were caused by differences in atmospheric pressure. In such an example, the atmospheric pressure in the geographic location in which the measurement is being conducted can be taken into account in determining the pressure. As another example, differences in temperature at the location in which the passive acoustic element(s) 106 are placed can have an effect on the measured pressure.

In some embodiments, the frequency or frequencies that excite the passive acoustic element(s) 106 can be measured at one or more known pressures, and these measurements can be used to calibrate pressures determinations made when the passive acoustic element(s) 106 are installed (e.g., implanted in a subject).

In some embodiments, material filling the passive acoustic element(s) 106 can escape from the passive acoustic element over time. For example, a gas filling the passive acoustic element(s) 106 can diffuse through the surrounding material 104. In such an example, the frequency response of the passive acoustic element(s) 106 may change over time as the density of the gas in the passive acoustic element(s) 106 decreases due to the diffusion of the gas. In some embodiments, determinations of the pressure based on a frequency of a signal emitted by the passive acoustic element(s) 106 (e.g., in response to excitation of the passive acoustic element(s)) can be modified based on the age of the passive acoustic element(s) 106.

In some embodiments, the resonance frequency of the passive acoustic element(s) 106 can change based on the characteristics of the material surrounding the passive acoustic element(s) 106, and/or based on the material(s) filling the passive acoustic element(s) 106. In some cases, the properties of the material surrounding the passive acoustic element(s) 106 can change over time when the composition of the surrounding material 104 changes as material accretes to the surrounding material 104 (e.g., mineral deposits, scar tissue, etc.). For example, if material accretes to the outside of a tube (e.g., a shunt) in which the passive acoustic element(s) are placed, a resonance frequency of the passive acoustic element(s) 106 can change as the material accretes. More particularly, in some embodiments, as the shear modulus (sometimes referred to as "G") of the combination of the surrounding material 104 and any accretions increases, the frequency of an emitted signal can tend to increase due to changes in the shear modulus of the surrounding material (e.g., due to the combined surrounding material being less flexible). Additionally, in some embodiments, as the bulk modulus (sometimes referred to as "K") of the combination of the surrounding material 104 and any accretions increases, the frequency of an emitted signal can tend to increase due to changes in the bulk modulus of the surrounding material (e.g., due to the combined surrounding material being less compressible). In some embodiments, increasing the size and/or length of the passive acoustic element(s) can decrease the size of the effect that changes in the surrounding material 104 and accretions have on the frequency of signals emitted by the passive acoustic element(s) 106. Additionally or alternatively, increasing the length of the passive acoustic element(s) 106 can increase the magnitude of the bulk response of the material (e.g., gas) in the passive acoustic element(s) 106, which can decrease the relative size of the effect caused by changes in the surrounding material 104 and accretions. Additionally or alternatively, in some embodiments, the characteristics of the surrounding material 104 can change over time, which can change the resonance frequency of the passive acoustic element(s) 106. For example, surrounding material 104 become less flexible over time.

In some embodiments, the surrounding material 104 can be a material with an acoustic impedance that is similar to the acoustic impedance of the passive acoustic elements 106 at a frequency or range of frequencies at which the passive acoustic elements are configured to be used. In such embodiments, matching the acoustic impedance can reduce the amount of reflection of the received acoustic signal as it passes through the interface between the surrounding material 104 and the passive acoustic element 106. While it may not be possible to obtain the best impedance match for each and every application due to practical constraints in the choice of the material(s) forming the surrounding material 104 and the passive acoustic element 106, impedance matching to the extent that it is possible can improve sensor performance and/or decrease the power required for the received acoustic signal to generate a response in the passive acoustic elements 106, as less of the power in the received signal is lost to reflections at the interface of the surrounding material 104 and the passive acoustic element 106. Similarly, in some embodiments, the surrounding material 104 and/or the passive acoustic elements 106 can be materials with acoustic impedances that are similar to the acoustic impedance(s) of materials in which the passive pressure sensor device 102 is placed in a frequency or range of frequencies at which the passive acoustic elements 106 are configured to be used.

In some embodiments, two or more different passive acoustic elements 106 in the passive pressure sensor device 102 can have different properties. For example, a first passive acoustic element 106 can be filled with a first amount of a first gas, and a second passive acoustic element 106 can be filled with a second amount of the first gas, with a first amount of a second gas, with a gel, with a fluid, etc. In some embodiments, using different materials for different passive acoustic elements 106 can provide independent measurements which may allow a user to interpret the likelihood that the measurements are accurate. Additionally, in some embodiments, providing different passive acoustic elements 106 in a passive pressure sensor device 102 that may be disposed in a variety of materials can facilitate the use of the passive acoustic elements at frequencies suited to those materials. Further, in some embodiments, using different materials and/or other characteristics for different passive acoustic elements 106 can provide a mechanism for differentiating passive acoustic elements 106 that are situated in a similar physical location. For example, a first passive acoustic element can be configured to operate in the range of 200 to 800 Hz, and a nearby passive acoustic element can be configured to operate in the range of 2 kHz to 8 kHz. In such an example, the value of the frequency of the response signal received can indicate which passive acoustic element responded to the input frequency.

In some embodiments, the surrounding material 104 can be a relatively compliant material, a relatively rigid material, or any suitable combination thereof. For example, in some embodiments, the surrounding material 104 can be a rigid material, such as glass, Pyrex™, silicon, metal, boron nitride, plastic, etc. As another example, in some embodiments, the surrounding material 104 can be a compliant material, such as, one or more suitable silicone rubbers (e.g., Cenusil®, Elsatosil®, Powersil®, Semicosil®, Silpuran®, Wacker®, etc.), one or more suitable Polyurethane rubbers (e.g., 6400 Polyurethane rubber, 6410 Polyurethane rubber, RTV60, etc.).

Additionally or alternatively, in some embodiments, the surrounding material 104 can be a biocompatible material, such as Echothane CPC-41, Echothane CPC-29, any other suitable biocompatible material, or any suitable combination thereof. In some embodiments, such biocompatible materials have acoustic impedance values (e.g., in the ultrasound range) which may be an acceptable match to the acoustic impedance of certain types of tissue and/or certain materials which can be used to fill the passive acoustic elements 106 (e.g., water). In some embodiments, such as in cases where the passive acoustic sensor device 102 is to be implanted in humans and/or other mammals, the material can be treated, surrounded, and/or impregnated with substances (e.g., antimicrobial drugs, antimicrobial materials, anticoagulants, etc.) which may decrease the risks of side effects from implantation.

Although the surrounding material 104 and the passive acoustic elements 106 are described herein in connection with specific materials, these are merely provided as examples. It is noted that the surrounding material 104 and/or the passive acoustic elements 106 can be made from, and/or can include, any suitable materials, and the thickness, dimensions, and/or composition of the surrounding material 104 and/or the passive acoustic elements 106 can be varied according to, inter alia, the sensor's specific design, the desired sensor performance, the medium in which the sensor is disposed during use, the pressure and temperature ranges within which the sensor is expected to operate, and/or any other manufacturing, construction parameters, and considerations.

Figure 2:
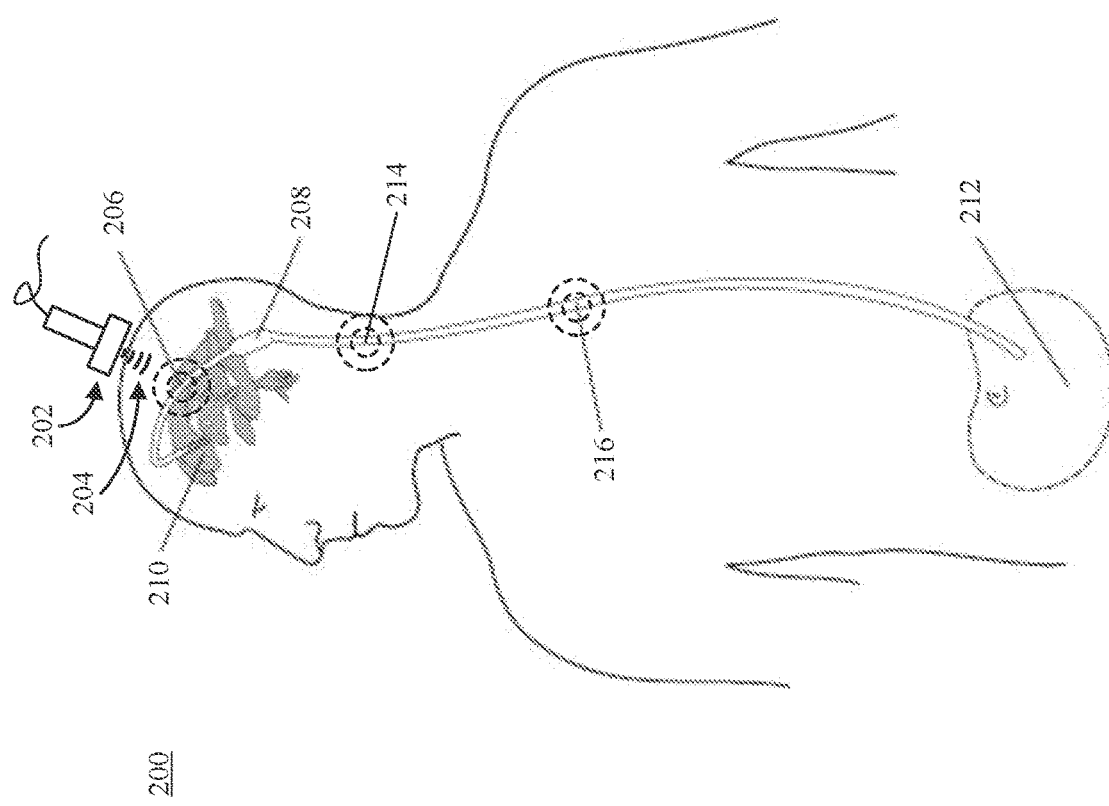
FIG. 2 shows an example of a system for measuring pressure in a ventriculoperitoneal shunt in accordance with some embodiments of the disclosed subject matter.

FIG. 2 shows an example 200 of a system for measuring pressure in a ventriculoperitoneal ("VP") shunt in accordance with some embodiments of the disclosed subject matter. As shown in FIG. 2, a pressure sensor interrogation device 202 can emit an applied signal(s) 204 toward a first location 206 in a VP shunt 208 that provides a conduit for CSF to flow from ventricles 210 and/or other areas in the brain of a subject through at least one lumen. In some embodiments, the VP shunt 208 can provide a conduit for CSF to flow from the ventricles 210 to the peritoneal cavity 212 of the subject. Note that this is merely an example, and a shunt can be placed to provide for the flow of CSF to any suitable area of the body of the subject, such as a cyst. In some embodiments, the applied signal 204 can be a signal in the acoustic range that is emitted by a speaker that is in contact with the subject's head, or otherwise near the subject's head.

In some embodiments, (e.g., as shown in FIG. 2), the applied signal 204 can be transmitted through the subject's skull, cerebrospinal fluid, brain, etc., and any surrounding material 104, to at least one passive acoustic element 106 implanted at the first location 206. In such embodiments, the pressure sensor interrogation device 202 can generate electrical signals (e.g., using a microphone) that can include electric signals caused by a detected response signal (not shown) generated by the passive acoustic element 106 implanted at the first location 206 that received the applied signal 204.

In some embodiments, the pressure sensor interrogation device 202 can calculate the pressure at the first location based on the frequency of the response signal generated by the passive acoustic element 106. In such embodiments, the pressure sensor interrogation device 202 can present the calculated pressure, using, for example, an integrated display and/or a display connected to the pressure sensor interrogation device (e.g., connected by wire, wirelessly, etc.). Additionally or alternatively, in some embodiments, the pressure sensor interrogation device 202 can output a signal indicating the frequency of the response signal to another device. For example, the pressure sensor can output the signal to a server, a personal computer, a laptop computer, a smartphone, a tablet computer, etc., which can then calculate the pressure at the first location 206.

In some embodiments, a pressure at the location 206 calculated by the pressure sensor interrogation device 202 and/or another computing device can be used to determine the likelihood that the VP shunt 208 is operating to drain CSF from the subject's ventricles 210. Additionally or alternatively, in some embodiments, the pressure sensor interrogation device 202 and/or another computing device can indicate whether the pressure at the location 206 is within a normal range, outside a normal range, whether the pressure is dangerous, whether the pressure indicates that the subject's hydrocephaly is being relieved by the VP shunt 208.

In some embodiments, pressure sensor interrogation device 202 can be used at other locations along the VP shunt 208 to determine whether there are differences in pressure along the VP shunt 208, which may be used to determine the patency of the shunt. For example, a comparison of the pressures at the first location 206, a second location 214 and a third location 216 may indicate whether, where, and/or to what extent the VP shunt is obstructed. In some embodiments, the characteristics (e.g., frequency range, power, etc.) of the applied signal 204 used to interrogate the passive acoustic element(s) 106 at the first location 206 can be the same or different than the applied signal used to interrogate the passive acoustic element(s) 106 at the second location 214 and/or the third location 216. For example, the applied signal(s) 204 used to interrogate the passive acoustic element(s) 106 implanted at the first location 206 can be in a first frequency range that is suited to transmission through the subjects skull, etc., while the applied signal(s) used to interrogate the passive acoustic element(s) 106 implanted at the third location 214 can have a second frequency range suited to transmission through the subject's chest. In such an example, the passive acoustic element(s) 106 implanted at the first location 206 and the third location 214 can have different characteristics that correspond to the frequency of the applied signal used to interrogate the passive acoustic element(s) 106. In a more particular example, the passive acoustic element(s) 106 implanted at the second location 214 can be configured to operate in a first frequency range, and the passive acoustic element(s) 106 implanted at the third location 216 can be configured to operate in a second frequency range that does not overlap with the first frequency range. In such a more particular example, the frequency of the response signal can be used to determine whether the response signal was generated by a passive acoustic element at the second location 214 or the third location 216 based on which range the response signal falls in. Note that, although FIG. 2 is described in connection with VP shunt 210, this is merely an example, and the mechanisms described herein can be used in a variety of applications, such as in subdural shunts, lumbar shunts, catheters, etc.

Figure 3:
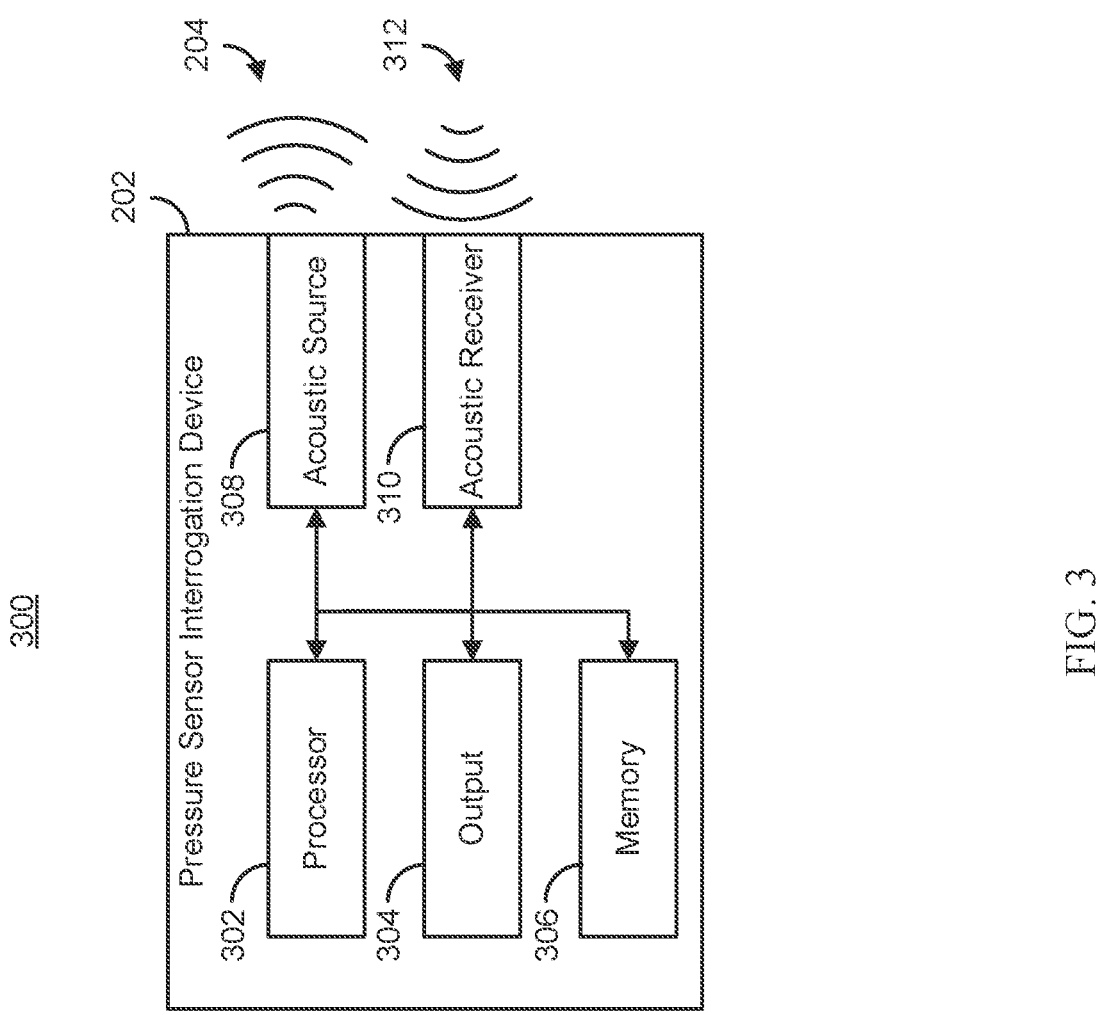
FIG. 3 shows an example of hardware that can be used to implement the pressure sensor interrogation device in connection with FIG. 2 in accordance with some embodiments of the disclosed subject matter.

FIG. 3 shows an example 300 of hardware that can be used to implement the pressure sensor interrogation device 202 described above in connection with FIG. 2 in accordance with some embodiments of the disclosed subject matter. As shown in FIG. 3, the pressure sensor interrogation device 202 can include a processor 302, one or more outputs 304, memory 306, one or more acoustic sources 308, and one or more acoustic receivers 310. In some embodiments, the processor 302 can be any suitable hardware processor or combination of processors, such as a central processing unit, a graphics processing unit, etc. In some embodiments, the one or more outputs 304 can include any suitable outputs such as a wire or cable (e.g., an audio cable, an Ethernet cable, etc.), a wireless transmitter and/or transceiver (e.g., a Bluetooth transceiver, a Wi-Fi transceiver, an infrared transmitter, etc.). Additionally or alternatively, in some embodiments, the one or more outputs 304 can include any suitable display or combination of displays, such as an LCD display, an LED display, a liquid crystal display, etc.

In some embodiments, memory 306 can include any suitable storage device or devices that can be used to store instructions, values, etc., that can be used, for example, by processor 302 to operate the acoustic source(s) 308 and/or the acoustic receiver(s) 310, to output signal via output(s) 304, etc. Memory 306 can include any suitable volatile memory, non-volatile memory, storage, or any suitable combination thereof. For example, memory 306 can include RAM, ROM, EEPROM, one or more flash drives, one or more hard disks, one or more solid state drives, one or more optical drives, etc. In some embodiments, memory 306 can have encoded thereon a computer program for controlling operation of the pressure sensor interrogation device 202. In such embodiments, the processor 302 can execute at least a portion of the computer program to interrogate passive acoustic elements (e.g., passive acoustic elements 106) embedded in other materials, calculate the pressure at the passive acoustic element(s) 106, present the pressure measured by interrogating the passive acoustic element(s) 106, etc.

In some embodiments, the one or more acoustic sources 308 can include any suitable device or devices that can be configured to emit acoustic signals, such as a speaker, an ultrasound transmitter, an ultrasound transceiver, etc. The one or more acoustic sources 308 can emit the applied signal(s) 204 based on one or more signals received from, for example, the processor 302. For example, the acoustic source 308 can receive an analog or digital signal from processor 302 that cause the acoustic source to emit a signal or signals at a frequency or frequencies that depends on the value(s) of the analog signal or the value(s) encoded in the digital signal. As another example, the acoustic source 308 can receive a control signal from the processor 302 that causes the acoustic source to emit a signal at a frequency that is determined by the hardware of the acoustic source 308 (e.g., the acoustic source can be a source that emits a signal with a predetermined frequency). For example, in some embodiments, processor 302 can control the acoustic source(s) 308 to emit signals at a series of frequencies to sweep a range of frequencies in which a passive acoustic element for which pressure is to be determined is configured to operate.

In some embodiments, the one or more acoustic sources 308 can be omitted and another source can be used to provide the applied signal 204. For example, a separate physical source of an acoustic signal, such as a tuning fork, can be used as an acoustic source. As another example, an internal source can be used to provide the applied signal 204, such as the subject's voice (e.g., humming, singing, talking, etc.), the subject's heartbeat, the subject's respiration, vibrations generated in the subject's skeletal system (e.g., as the subject walks), any other suitable internal source, or any suitable combination thereof.

In some embodiments, the one or more acoustic receivers 310 can include any suitable device or devices that can be configured to generate an electrical signal with a value based on a response signal 312 that was emitted by a passive acoustic element 106, such as a microphone, a hydrophone, an ultrasound receiver, an ultrasound transceiver, a surface acoustic wave receiver, etc. The one or more acoustic receivers can detect sound waves and generate an analog and/or digital signal, which can be output to the processor 302 and/or the output 304.

Note that, although the acoustic source(s) 308 and the acoustic receiver(s) 310 are shown in FIG. 3 as being integrated in a single device, this is merely an example, and the acoustic source(s) 308 and the acoustic receiver(s) 310 can be separate devices that can be separately brought into proximity to a subject to measure the pressure at one or more passive acoustic elements 106 within the subject.

Figure 4A:
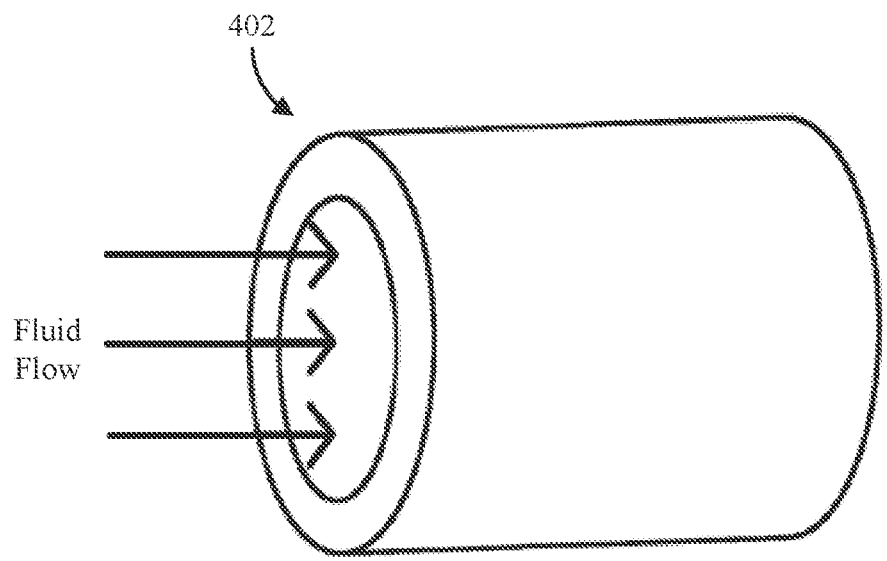
FIGS. 4A and 4B show an example of a tube with passive acoustic elements present within walls of the tube in accordance with some embodiments of the disclosed subject matter.
Figure 4B:
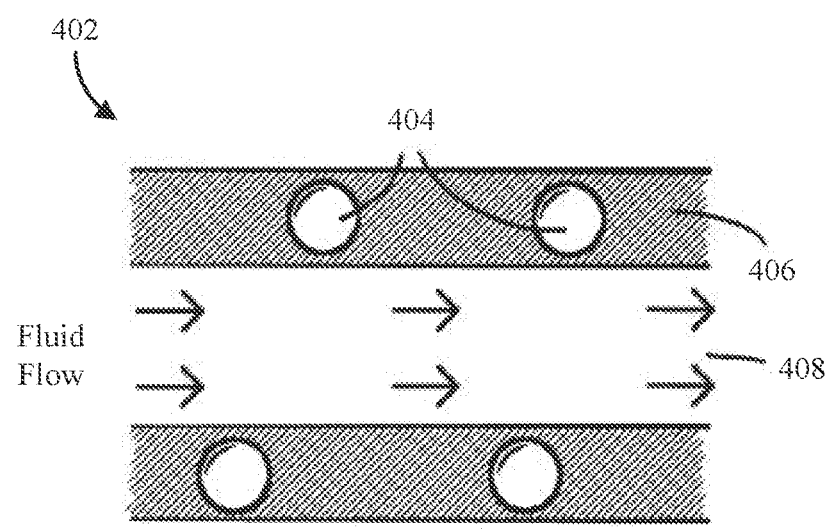

FIGS. 4A and 4B show an example of a tube 402 with passive acoustic elements 404 present within walls 406 of the tube 402 in accordance with some embodiments of the disclosed subject matter. As shown in FIGS. 4A and 4B, the passive acoustic elements 404 can be interrogated to determine the pressure of fluid 408 present within the tube. In some embodiments, the passive acoustic elements 404 can be present within the walls of the VP shunt 208 described above in connection with FIG. 2. In such embodiments, the passive acoustic elements 404 can be formed within the walls 406 and/or can be formed and inserted into the walls 406 during fabrication of the walls 406. In some embodiments, any suitable number of passive acoustic elements 404 can be present within the walls 406 at any suitable location or locations. For example, in some embodiments, the passive acoustic elements 404 can be present within the walls 406 of the tube 402 along the entire length of the tube. As another example, in some embodiments, the passive acoustic elements 404 can be present within the walls 406 of the tube 402 at particular locations, such as locations that are commonly of interest in determining how well the tube is performing a particular function. Note that passive acoustic elements can be present in any suitable portion of a shunt, such as valves, reservoirs, anti-siphon devices, etc.

Figure 5:
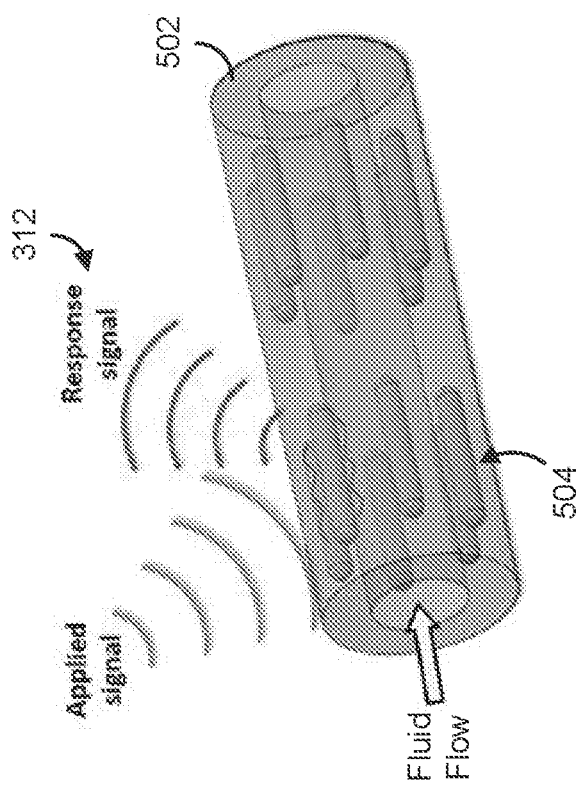
FIG. 5 shows an example of a tube with passive acoustic elements having an elongate shape present within walls of the tube in accordance with some embodiments of the disclosed subject matter.

FIG. 5 shows an example of a tube 502 with passive acoustic elements 504 having an elongate shape present within the walls of the tube 502 in accordance with some embodiments of the disclosed subject matter. As described above in connection with FIGS. 4A and 4B, passive acoustic elements 504 can be interrogated to determine the pressure of fluid within the tube 502. In some embodiments, tube 502, or any other similar tube, can be made by extrusion of a catheter having two or more lumens, with one or more of the lumens other than a lumen through which fluid is to flow being blocked with material periodically.

Figure 6:
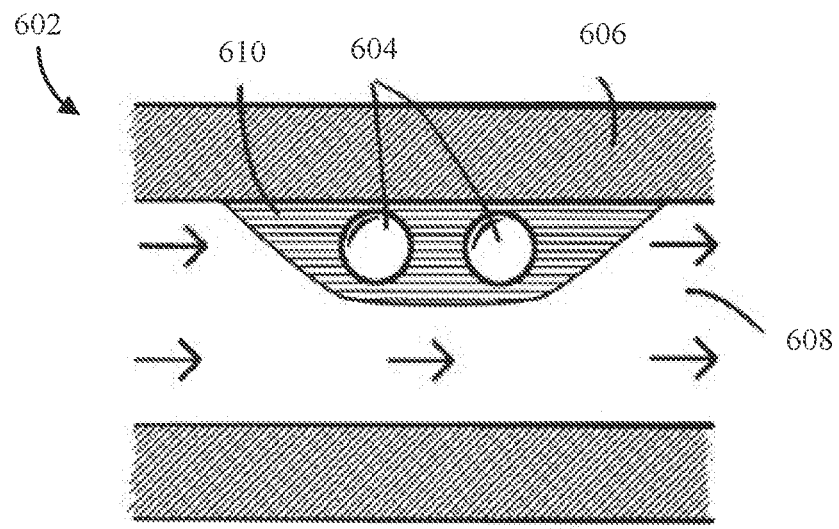
FIG. 6 shows an example of a tube with passive acoustic elements present in a surrounding material, which is attached to an interior wall of the tubing in accordance with some embodiments of the disclosed subject matter.

FIG. 6 shows an example of a tube 602 with passive acoustic elements 604 present in a surrounding material 610, which is attached to an interior wall 606 of the tubing in accordance with some embodiments of the disclosed subject matter. As described above in connection with FIGS. 4A and 4B, passive acoustic elements 604 can be interrogated to determine the pressure of fluid 608 within the tube 602. In some embodiments, the passive acoustic elements 604 can be present along the entire length of the tube 602. In such embodiments, the surrounding material 610 can be present along the entire length of the tube 602 or can be present in discrete sections. Additionally, in such embodiments, the surrounding material 610 can be present along the entire interior circumference of the tube 602 or can be present along a particular portion of the interior of the tube 602.

Figure 7:
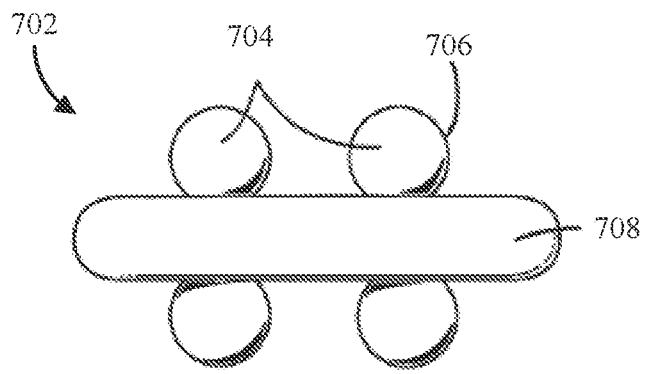
FIG. 7 shows another example of a passive pressure sensor device in accordance with some embodiments of the disclosed subject matter.

FIG. 7 shows another example of a passive pressure sensor device 702 in accordance with some embodiments of the disclosed subject matter. As shown in FIG. 7, in some embodiments, several passive acoustic elements 704 formed within respective membranes 706 can be attached to a base element 708. In such embodiments, the base element 708 and/or the passive acoustic elements can be attached to the inside of a tube (e.g., VP shunt 208), placed within a container where it can move about freely, placed within a body cavity (the cranial vault of a subject, the kidney of a subject, etc.), swallowed, etc. In some embodiments, any suitable number of passive pressure sensor devices 702 can be used to measure the pressure of a material within which it is disposed.

Figure 8:
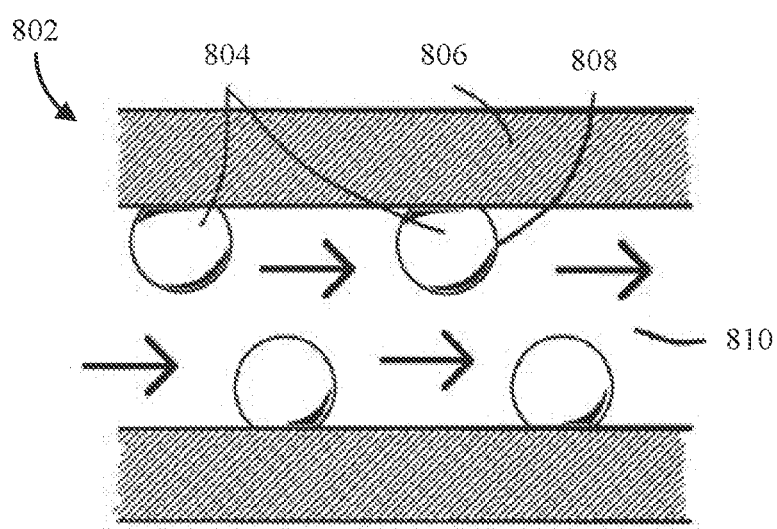
FIG. 8 shows an example of a tube with passive acoustic elements formed within respective membranes attached to the inside of a wall in accordance with some embodiments of the disclosed subject matter.

FIG. 8 shows an example of a tube 802 with passive acoustic elements 804 formed within respective membranes 808 attached to the inside of a wall 806 in accordance with some embodiments of the disclosed subject matter. As described above in connection with FIGS. 4A and 4B, passive acoustic elements 804 can be interrogated to determine the pressure of fluid 810 within the tube 802. In some embodiments, the passive acoustic elements 804 can be present along the entire length of the tube 802. In such embodiments, the surrounding material 810 can be present along the entire length of the tube 802 or can be present in discrete sections. Additionally, in such embodiments, the surrounding material 810 can be present along the entire interior circumference of the tube 802 or can be present along a particular side of the interior of the tube 802.

Figure 9:
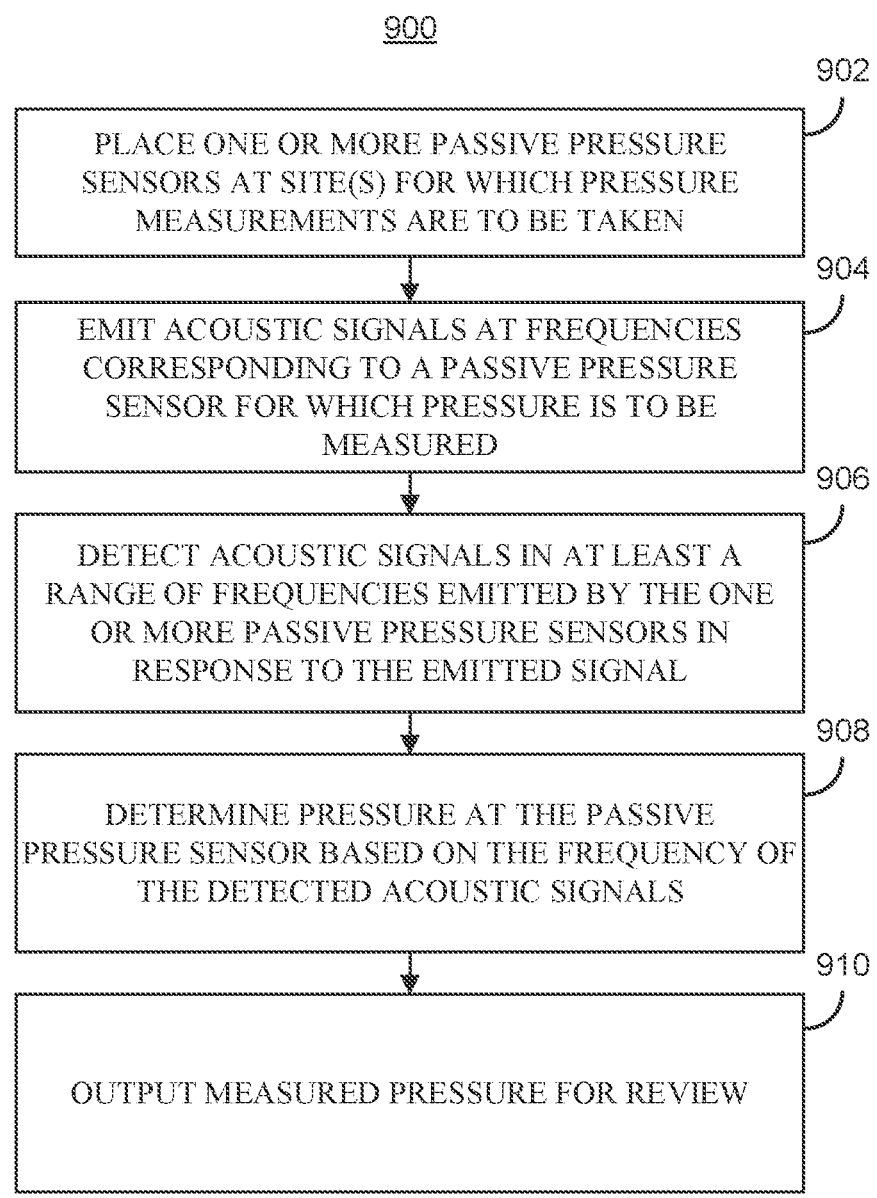
FIG. 9 shows an example of a process for remotely measuring pressure in a location using one or more passive pressure sensors in accordance with some embodiments of the disclosed subject matter.

FIG. 9 shows an example 900 of a process for remotely measuring pressure in a location using one or more passive pressure sensors in accordance with some embodiments of the disclosed subject matter. As shown in FIG. 9, at 902, one or more passive pressure sensors can be placed at one or more sites for which pressure measurements are to be taken. In some embodiments, the one or more passive pressure sensors can be passive pressure sensing devices (e.g., passive pressure sensing device 102, passive pressure sensing device 702) that include one or more passive acoustic elements (e.g., as described above in connection with FIGS. 1A and 1B, 4A and 4B, and 5-8). Additionally or alternatively, the one or more passive pressure sensors can be passive acoustic elements (e.g., as described above in connection with FIGS. 1A and 1B, 4A and 4B, and 5-8). In some embodiments, the one or more passive pressure sensors can be placed using any suitable technique or combination of techniques. For example, in some embodiments, the one or more passive pressure sensors can be located within (and/or attached to) the wall of a tube, such as a shunt or catheter, which can be implanted within a subject (e.g., surgically).

In some embodiments, before placing the passive pressure sensors at 902, the frequency response under one or more known conditions can be measured to calibrate calculations based on signals emitted from the passive pressure sensors. The values determined through this calibration can be recorded and used in determining pressure of the passive pressure sensor (e.g., as described below in connection with 908).

At 904, process 900 can cause a pressure sensor interrogation device (e.g., pressure sensor interrogation device 202) to emit one or more acoustic signals (e.g., an applied signal as described above in connection with FIG. 2) at frequencies corresponding to a range of frequencies for which a passive pressure sensor (e.g., a passive pressure sensor placed at 902) for which pressure is to be determined is configured to operate. In some embodiments, process 900 can cause the pressure sensor interrogation device to emit the applied signals in response to any suitable input. For example, a user can power on the pressure sensor interrogation device. As another example, process 900 can cause the pressure sensor interrogation device to emit the applied signal in response to a user input. In some embodiments, the pressure sensor interrogation device can use any suitable device or combination of devices to emit the applied signals, such as an acoustic source 308 described above in connection with FIG. 3.

At 906, process 900 can cause the pressure sensor interrogation device to detect acoustic signals (e.g., response signals) in at least a range of frequencies emitted by the one or more pressure sensors placed at 902. In some embodiments, process 900 can use any suitable device or combination of devices to detect the response signals, such as an acoustic receiver 310 described above in connection with FIG. 3.

At 908, process 900 can determine the pressure at the one or more passive pressure sensors that emitted the response signal(s) based on the frequency of the detected acoustic signals. In some embodiments, process 900 can cause the pressure sensor interrogation device to determine a frequency or frequencies at which a response signal was received, and can calculate the pressure based on the value of the frequency. For example, the pressure sensor interrogation device can determine a correlation between the frequency and pressure at the one or more passive pressure sensors (e.g., e.g., using a look up table, using an equation, etc.). In some embodiments, the pressure sensor interrogation device can determine the pressure based on one or more parameters other than the frequency of the response signal, such as the material(s) filling the one or more passive pressure sensors, the temperature of the one or more passive pressure sensors, atmospheric pressure, calibration values for the passive pressure sensors being interrogated, etc.

In some embodiments, another device (e.g., a computing device) can determine the pressure based on the frequency of the response signal, calibration data (e.g., determined prior to placing the passive pressure sensor(s)), ambient pressure, temperature, any other suitable information, or any suitable combination thereof.

At 910, process 900 can cause the measured pressure to be output for review using any suitable technique or combination of techniques. For example, in some embodiments, process 900 can cause the pressure sensor interrogation device to present the calculated pressure on a display. As another example, process 900 can cause the computing device that determined the pressure to present the pressure on a display. As yet another example, process 900 can cause the pressure to be transmitted to a particular computing device and/or a particular address (e.g., email address, IP address, etc.). In a more particular example, process 900 can cause the pressure to be transmitted to the computing device only in cases in which the pressure is outside of a "normal" range (e.g., as defined by a surgeon, engineer, etc.).

In some embodiments, a passive pressure sensor device (e.g., passive pressure sensor device 102, passive pressure sensor device 702), can be secured in place using a clamp, a hook, a suture, any other suitable technique for securing it such that remains fixed in one area, and/or any other suitable technique. Further, in some embodiments, the passive pressure sensor device can be implemented such that the sensor is formed as part of a sensor anchoring device and/or may be formed within a sensor anchoring device. Such sensor anchoring device can be, for example, a sensor positioner, an implantable graft, any suitable part of an implantable device, a pacemaker, a defibrillator or a part thereof, an implantable electrode or a part thereof, an insertable electrode or a part thereof, an implantable catheter or a part thereof, an insertable catheter or a part thereof, a stent, a part of a stent, a guide-wire or a part thereof, an endoscopic device or a part thereof, an autonomous or tethered endoscopic device or a part thereof, any other suitable type of implant, and/or any other suitable device which can be implanted in, or inserted into, a body of any organism, animal, and/or human patient. Additionally, in some embodiments, a passive pressure sensor device (e.g., passive pressure sensor device 102, passive pressure sensor device 702) can be secured in place using one or more mechanical fasteners (e.g., screws, bolts, wire, etc.), one or more adhesives, etc.

Note that the sensor anchoring devices described above to which the passive acoustic sensors of the present disclosure can be attached (or within which anchoring device the passive acoustic sensors can be formed or included as a part thereof), are not limited to devices having the sole purpose of serving as a support or carrying platform for the protected sensor of the present disclosure. Rather, the anchoring devices can have any other suitable structure and/or function that may or may not be related to the structure or function(s) of the protected sensor, and can also be used for other unrelated purposes besides functioning as a support for the protected sensor. For example, if a passive acoustic sensor is attached to, formed within, or enclosed in, a tube of a catheter or shunt, the tube can function as a platform or member for carrying or holding the passive pressure sensor device 102 and/or passive acoustic element(s) 106, while independently functioning as a drainage tube. Thus, the attachment of the passive acoustic sensors of the present disclosure to any device that can be positioned in a measurement environment (or the inclusion thereof in such a device) can, but need not necessarily be associated with the functioning of the device.

Similarly, a sealed chamber of the passive acoustic sensors of the present disclosure can be formed within any such suitable sensor anchoring device or sensor supporting device or sensor fixating devices, or implantable grafts or other type of implant or implantable device. The surrounding material of the passive acoustic sensors of the present disclosure can also be configured to comprise a part or as a portion of any such suitable sensor anchoring device or sensor supporting device or sensor fixating devices, or implantable grafts or any other type of an implant or implantable device or stent, as a part of the sealed chamber.

Further, the devices described herein can be built either with any suitable types of attachment points built in, or with grooves, holes or other geometrical features that can facilitate attachment of the device to the targeted area.

Figure 10:
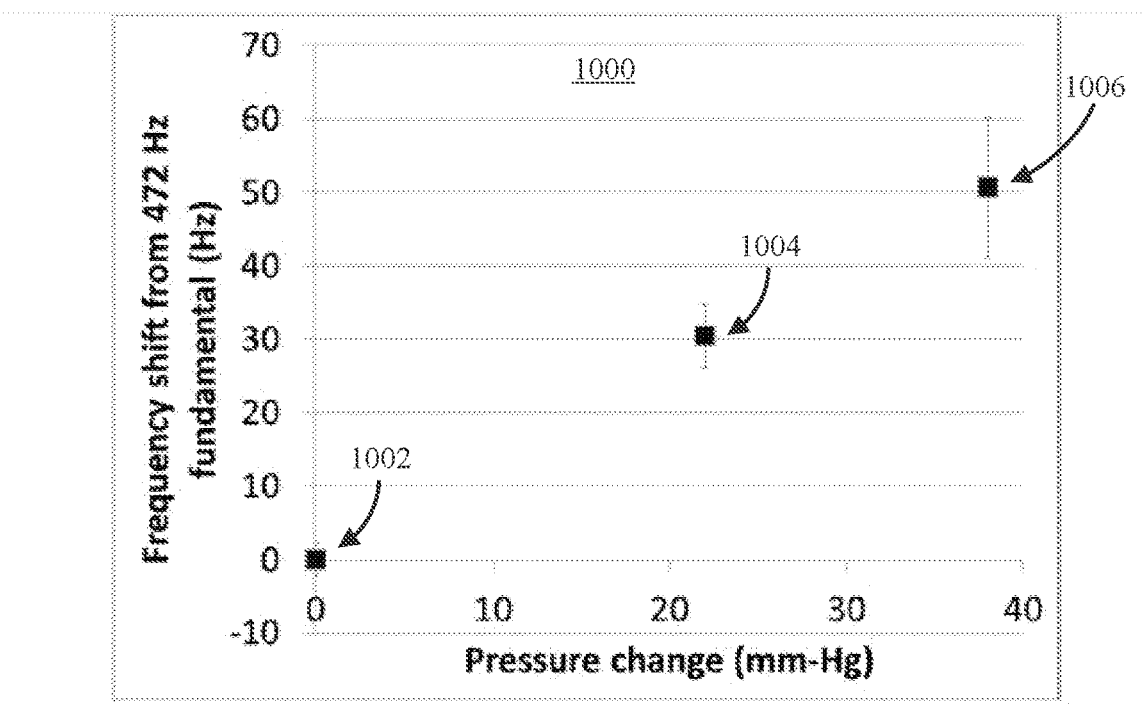
FIG. 10 shows an example of a plot showing changes in a frequency of a response signal with changes in pressure in accordance with some embodiments of the disclosed subject matter.

FIG. 10 shows an example 1000 of a plot showing changes in a frequency of a response signal with changes in pressure in accordance with some embodiments of the disclosed subject matter. Plot 1000 represents the frequencies at which the passive pressure sensor devices having at least one passive acoustic element that is filled with gas responds when submerged in a container filled with various amounts of water to change the pressure on the passive pressure sensor device. As shown in FIG. 10, at a baseline pressure 1002, the passive pressure sensor devices respond to a signal at 472 Hz. As the pressure increases (e.g., as more water is added to the container), at a second pressure 1004 that is about twenty-two mm-Hg higher than the baseline pressure, the passive pressure sensor devices respond to a signal at about 502 Hz. As the pressure increases further, at a third pressure 1006 that is about thirty-eight mm-Hg higher than the baseline pressure, the passive pressure sensor devices respond to a signal at about 522 Hz.

Figure 11:
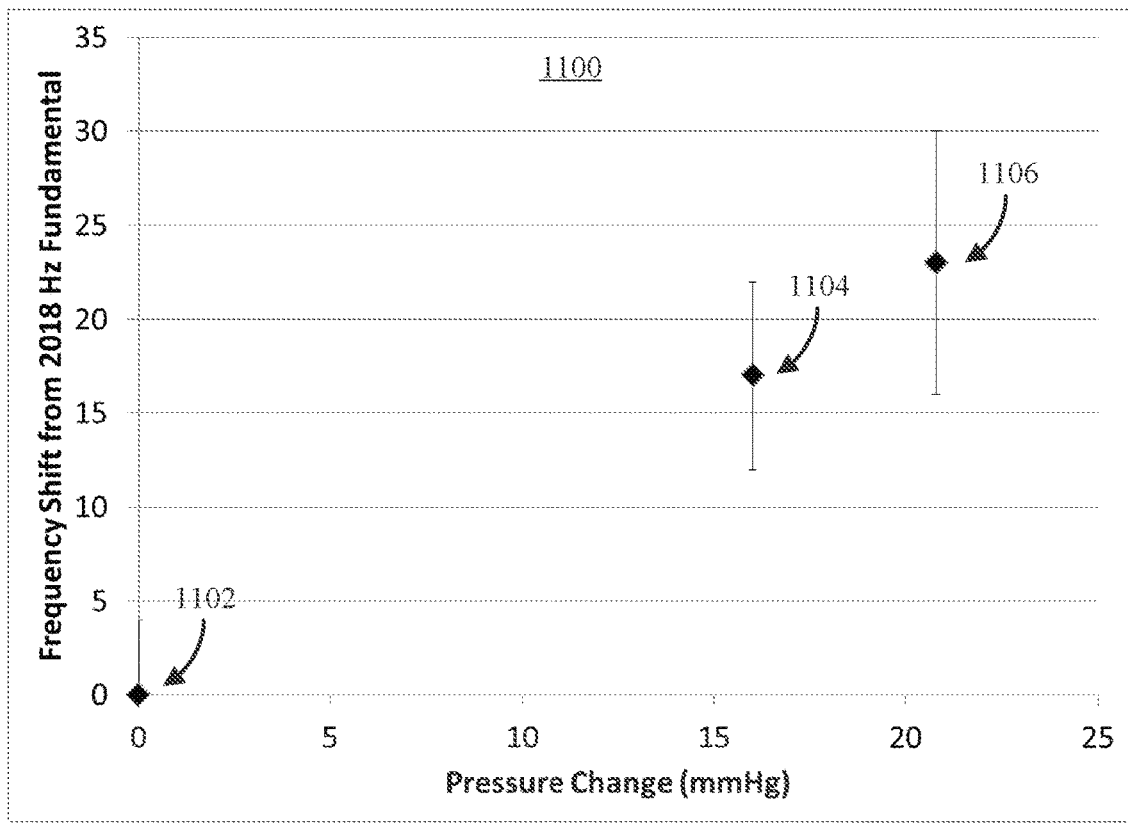
FIG. 11 shows another example of a plot showing changes in a frequency of a response signal with changes in pressure in accordance with some embodiments of the disclosed subject matter.

FIG. 11 shows another example 1100 of a plot showing changes in a frequency of a response signal with changes in pressure in accordance with some embodiments of the disclosed subject matter. Plot 1100 represents the frequencies at which the passive pressure sensor devices that each include a gas-filled passive acoustic element that can be approximated as a cylinder of about one mm in diameter by 30 mm in length responds when placed in cadaver goat test subjects and filled with liquid at various known pressures to vary the pressure exerted on the passive acoustic elements. As shown in FIG. 11, at a baseline pressure 1102 the passive pressure sensor devices respond to a signal at about 2,018 Hz. As the pressure increases, at a second pressure 1104 that is about seventeen mm-Hg higher than the baseline pressure, the passive pressure sensor devices respond to a signal at about 2,035 Hz. As the pressure increases further, at a third pressure 1106 that is about twenty-two mm-Hg higher than the baseline pressure, the passive pressure sensor devices respond to a signal at about 2,041 Hz.

Figure 12:
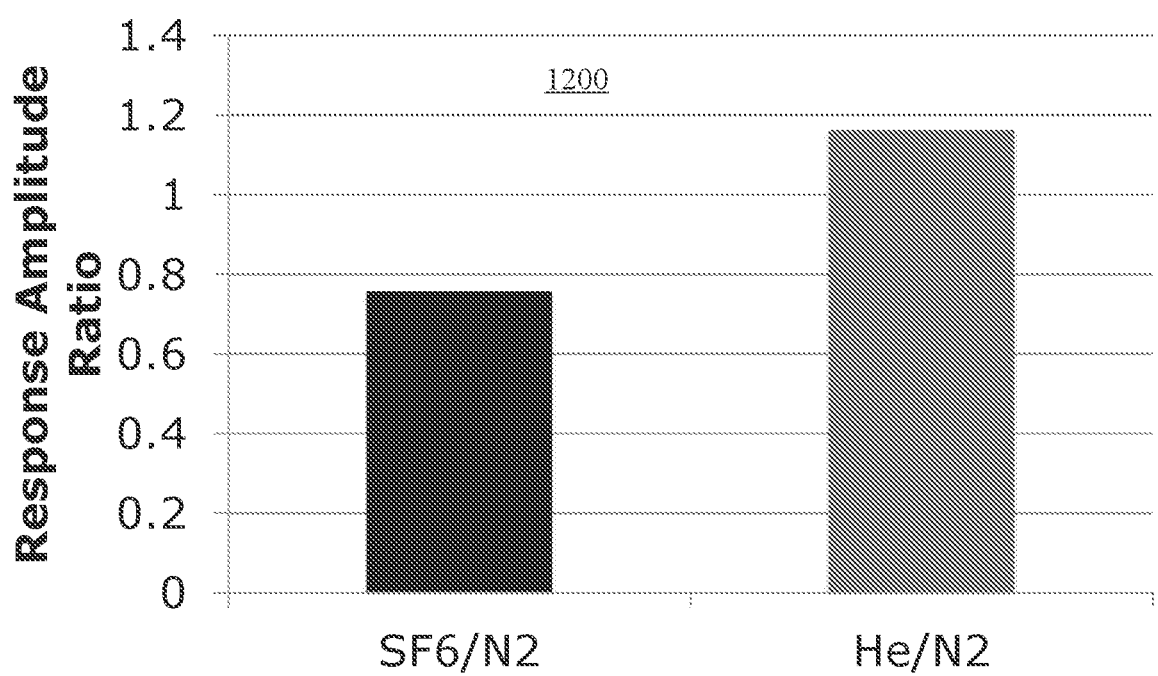
FIG. 12 shows an example of a plot showing difference in the amplitude of the response signal of different gases that can be used to fill passive acoustic elements in accordance with some embodiments of the disclosed subject matter.

FIG. 12 shows an example 1200 of a plot showing difference in the amplitude of the response signal of different gases that can be used to fill passive acoustic elements in accordance with some embodiments of the disclosed subject matter. As shown in plot 1200 in FIG. 12, sulfur hexafluoride provides a smaller amplitude response signal with respect to using nitrogen, whereas using helium provides a larger amplitude response signal with respect to both nitrogen and sulfur hexafluoride. These characteristics are at least partially due to the differences in atomic weight between the helium atoms, nitrogen molecules, and sulfur hexafluoride molecules, with lighter atomic weights reacting more strongly and creating a larger amplitude signal. However, heavier atomic weight gases are less likely to diffuse out of the passive acoustic elements and surrounding materials, which can limit the useful lifetime of the passive acoustic elements.

One skilled in the art will readily appreciate that the present invention is well adapted to carry out the objects and obtain the ends and advantages mentioned, as well as those inherent therein. The present embodiments described herein are representative of some embodiments of the disclosed subject matter, and are not intended as limitations on the scope of the invention. Changes therein and other uses will occur to those skilled in the art which are encompassed within the spirit of the invention as defined by the scope of the claims.

What is claimed is:

1. A system for determining pressure in a ventriculoperitoneal shunt implanted in an in vivo subject, the system comprising:
   an acoustic source that emits a plurality of first signals over a range of frequencies;
   the ventriculoperitoneal shunt, comprising:
      at least one lumen that provides a conduit for cerebrospinal fluid between an area of the subject's brain and a cavity within the body of the subject; and
      a passive acoustic element in a wall of the ventriculoperitoneal shunt comprising a void in the wall of the ventriculoperitoneal shunt that is filled with a gas, wherein the passive acoustic element emits a second signal at a resonant frequency that varies based on the pressure on the passive acoustic element in response to receiving a signal of the plurality of first signals at the resonant frequency;
   an acoustic receiver that detects the second signal and outputs an electrical signal that represents at least the resonant frequency; and
   at least one hardware processor that is programmed to:
      receive the electrical signal;
      determine the frequency of the second signal; and
      present information based on the frequency using a display.

2. The system of claim 1, wherein the passive acoustic element has a substantially spherical shape.

3. The system of claim 1, wherein the passive acoustic element has an elongate shape.

4. The system of claim 1, wherein the gas is comprised primarily of nitrogen gas.

5. The system of claim 1, wherein the ventriculoperitoneal shunt further comprises a second passive acoustic element, wherein the second passive acoustic element emits a third signal at a second resonant frequency that varies based on the pressure on the passive acoustic element in response to receiving a signal of the plurality of signals at the second resonant frequency, wherein the properties of the second passive acoustic element are different than the properties of the passive acoustic element,
   wherein the acoustic source emits a plurality of fourth signals over a second range of frequencies that does not overlap with the range of frequencies, and
   wherein the hardware processor is further programmed to:
      detect a third signal at a second resonant frequency;
      determine the pressure on the second passive acoustic element using at least the second resonant frequency.

6. The system of claim 1, wherein the acoustic source is a speaker and the first frequency is between 20 Hz and 20 kHz.

7. A method for determining pressure in a ventriculoperitoneal shunt implanted in an in vivo subject, the method comprising:
   emitting, using an acoustic source, a plurality of first signals over a range of frequencies toward the ventriculoperitoneal shunt, the ventriculoperitoneal shunt comprising:
      at least one lumen that provides a conduit for cerebrospinal fluid between an area of the subject's brain and a cavity within the body of the subject; and
      a passive acoustic element in a wall of the ventriculoperitoneal shunt comprising a void in the wall of the ventriculoperitoneal shunt that is filled with a gas, wherein the passive acoustic element emits a second signal at a resonant frequency that varies based on the pressure on the passive acoustic element in response to receiving a signal of the plurality of first signals at the resonant frequency;
   detecting, using an acoustic receiver, the second signal;
   output, using the acoustic receiver, an electrical signal that represents at least the resonant frequency;
   determining the frequency of the second signal; and
   presenting information based on the frequency using a display.

8. The method of claim 7, wherein the passive acoustic element has a substantially spherical shape.

9. The method of claim 7, wherein the passive acoustic element has an elongate shape.

10. The method of claim 7, wherein the gas is comprised primarily of nitrogen gas.

11. The method of claim 7, wherein determining the pressure further comprises:
   emitting, using the acoustic source, a plurality of fourth signals over a second range of frequencies that does not overlap with the range of frequencies toward the ventriculoperitoneal shunt, the ventriculoperitoneal shunt further comprising:
      a second passive acoustic element, wherein the second passive acoustic element emits a third signal at a second resonant frequency that varies based on the pressure on the passive acoustic element in response to receiving a signal of the plurality of signals at the second resonant frequency, wherein the properties of the second passive acoustic element are different than the properties of the passive acoustic element,
   detecting a third signal at a second resonant frequency;
   determining the pressure on the second passive acoustic element using at least the second resonant frequency.

12. The method of claim 7, wherein the acoustic source is a speaker and the first frequency is between 20 Hz and 20 kHz.

* * * * *